(12) United States Patent
Bhanu et al.

(10) Patent No.: US 12,270,802 B2
(45) Date of Patent: Apr. 8, 2025

(54) AGRICULTURAL MACHINE WITH RESONANCE VIBRATION RESPONSE DETECTION

(71) Applicant: Deere & Company, Moline, IL (US)

(72) Inventors: Mahesh N. Bhanu, Magarpatta (IN); Benjamin M. Smith, Falls Church, VA (US); Noel W. Anderson, Fargo, ND (US)

(73) Assignee: Deere & Company, Moline, IL (US)

( * ) Notice: Subject to any disclaimer, the term of this patent is extended or adjusted under 35 U.S.C. 154(b) by 836 days.

(21) Appl. No.: 16/114,916

(22) Filed: Aug. 28, 2018

(65) Prior Publication Data

US 2020/0072809 A1    Mar. 5, 2020

(51) Int. Cl.
*G01N 29/44*       (2006.01)
*A01B 79/00*       (2006.01)
(Continued)

(52) U.S. Cl.
CPC ....... *G01N 33/0098* (2013.01); *A01B 79/005* (2013.01); *B64U 20/87* (2023.01);
(Continued)

(58) Field of Classification Search
CPC ...... G01N 1/00; G01N 2201/00; A01B 71/02; A01B 79/005; A01D 91/04; A01G 7/06; A01M 21/00; A01M 7/0057; A01M 7/0089; B64C 2201/123; B64C 39/024; G05D 1/0246; G05D 2201/0201; G06K 9/00657
See application file for complete search history.

(56) References Cited

U.S. PATENT DOCUMENTS 5,152,401 A * 10/1992 Affeldt, Jr. ............. G01N 3/405
                                                     209/556
7,165,451 B1 * 1/2007 Brooks ................... A61N 5/00
                                                     73/579
(Continued)

FOREIGN PATENT DOCUMENTS

WO     WO 2018073481 A1    4/2018

OTHER PUBLICATIONS

Rolf J.Korneliussen, Acoustic identification of marine species using a feature library, Dec. 2016 (Year: 2016).*
(Continued)

*Primary Examiner* — Matthew J. Reda
(74) *Attorney, Agent, or Firm* — Christopher J. Volkmann; Kelly Holt and Christenson. PLLC

(57) ABSTRACT

An agricultural machine includes a vibration stimulation source configured to generate a vibration stimulation signal directed toward plant matter and a sensor system configured to sense electromagnetic radiation reflected from the plant matter, generate a first signal based on the sensed electromagnetic radiation, and generate a second signal indicative of a resonant vibration response of the plant matter, that is in response to the vibration stimulation signal. The agricultural machine includes a plant evaluation system configured to, based on the first and second signals, generate plant characterization data indicative of one or more physical characteristics of the plant matter, and a control system configured to generate an action signal based on the plant characterization data.

19 Claims, 11 Drawing Sheets

(51) Int. Cl.
| | |
|---|---|
| *B64U 20/87* | (2023.01) |
| *G01N 21/29* | (2006.01) |
| *G01N 29/34* | (2006.01) |
| *G01N 33/00* | (2006.01) |
| *G05D 1/00* | (2006.01) |
| *B64U 101/30* | (2023.01) |
| *B64U 101/40* | (2023.01) |

(52) U.S. Cl.
CPC .......... *G01N 21/29* (2013.01); *G01N 29/348* (2013.01); *G01N 29/4409* (2013.01); *G05D 1/0246* (2013.01); *B64U 2101/30* (2023.01); *B64U 2101/40* (2023.01); *G01N 2223/612* (2013.01)

(56) References Cited

U.S. PATENT DOCUMENTS

| | | | |
|---|---|---|---|
| 9,740,208 | B2 | 8/2017 | Sugumaran et al. |
| 9,963,817 | B2 | 5/2018 | McLean et al. |
| 2007/0039389 | A1* | 2/2007 | Brooks .................. A61B 8/00 73/579 |
| 2009/0158848 | A1* | 6/2009 | Brooks ................. A61B 5/417 73/579 |
| 2009/0217758 | A1* | 9/2009 | Loeser ................ G01N 29/222 73/573 |
| 2014/0154729 | A1* | 6/2014 | Leyns .................... G01N 21/17 435/29 |
| 2015/0245554 | A1 | 9/2015 | Redden |
| 2016/0000008 | A1* | 1/2016 | Scholer .............. A01D 41/1273 56/10.2 R |
| 2017/0031365 | A1 | 2/2017 | Sugumaran et al. |
| 2017/0071188 | A1* | 3/2017 | Rees ....................... G06K 9/52 |
| 2017/0228118 | A1 | 8/2017 | Sugumaran et al. |
| 2018/0153084 | A1* | 6/2018 | Calleija ............... A01B 63/004 |
| 2019/0191631 | A1* | 6/2019 | Regan .................. B64C 39/024 |
| 2019/0350140 | A1* | 11/2019 | Werner .................... A01G 7/04 |

OTHER PUBLICATIONS

Hartwig Schulz, Qualitative and Quantitative FT-Raman Analysis of Plants, Dec. 6, 2013 (Year: 2013).*

Iris Brémaud, Mechanical damping of wood as related to species classification: a preliminary survey, Apr. 5, 2013 (Year: 2013).*

Search Report issued in counterpart EP Application No. 19192523. 9, dated Jan. 29, 2020 (7 pages).

F.J. 'Pi nera-Chaveza, et al. "Avoiding lodging in irrigated spring wheat. I. Stem and root structural requirements", Journal homepage: www.elsevier.com/locate/fcr, Bearing a date of Jun. 30, 2016, 12 pages.

Motoaki Sano et al. "Estimation of water stress of plant by vibration measurement of leaf using acoustic radiation force", Acoust. Sci. & Tech. 36, 3 (Bearing a date of 2015), 6 pages.

Laser-Doppler Vibrometer Measurements of Leaves, https://link.springer.com/chapter/10.1007/978-3-642-83611-4_1, 6 pages. Springer Nature Switzerland AG. Part of Springer Nature. Bearing a date of 1990.

M.J.M. Martens "Laser-Doppler Vibrometer Measurements of Leaves" H.-F. Linskens et al. (eds.), Physical Methods in Plant Sciences © Springer-Verlag Berlin Heidelberg 1990. 2 pages.

Classifying plants with ultrasonic sensing. Neil Lindsay Harper and Phillip John MCKerrow, www.araa.asn.au/acra/acra1999/papers/paper31.pd, 6 pages 1999.

Manukain et al. "Plant Health Sensing", Fall 1987, 34 pages.

Dionisio Andújar et al., "An Ultrasonic System for Weed Detection in Cereal Crops", www.mdpi.com/journal/sensors, ISSN 1424-8220, Published: Dec. 13, 2012, 15 pages.

Davis, Abe "New Video Technology That Reveals An Object's Hidden Properties" Videohttps://www.ted.com/talks/abe_davis_new_video_technology_that reveals_an_object_s_hidden_properties Ted2015| Bearing a date of Mar. 2015.

Elgharib et al., "Video Magnification in Presence of Large Motion" Qatar Computing Research Institute MIT CSAIL 9 pages. 2015.

Polytec, "Introduction to 3-D Scanning Vibrometry", https.//www.youtube.com/watch?v=YWwZU2hgjs8, dated Feb. 25, 2009.

Rubinstein, Michael, "See invisible motion, hear silent sounds. Cool? Creepy? We can't decide", https://www.youtube.com/watch?v=fHfhorJnAEI&t, Dec. 23, 2014.

Magal, C. et al. "The Role of Leaf Structure In Vibration Propagation", 7 pages. 2000.

Physical Methods in Plant Sciences, 1990, 112 pages.

Nakagawa et al. "Basic study on the detection of the water stress in plant using ultrasonic sound source". Proceedings of Symposium on Ultrasonic Electronics vol. 36, Nov. 5-7, 2015, 2 pages.

"Ag Leader", retrieved at <http://www.agleader.com/products/directcommand/optrx-crop-sensors>, Available at least as of Aug. 27, 2018, 92 pages.

* cited by examiner

AGRICULTURAL MACHINE WITH RESONANCE VIBRATION RESPONSE DETECTION

FIELD OF THE DESCRIPTION

The present description generally relates to resonance vibration response detection of plant matter for an agricultural machine. More specifically, but not by limitation, the present description relates to an agricultural machine that uses resonance frequency detection to generate action control signals based on plant matter evaluations.

BACKGROUND

Agricultural machines are utilized for a wide variety of agricultural processes. For instance, agricultural machines can be utilized to plant crops, provide crop care operations (chemical spraying, watering, etc.), harvesting operations, to name a few. In traditional farming applications, an agricultural machine includes or otherwise supports an agricultural implement that can include tools for operation such as tillage, planting, spraying, baling, reaping, etc. In turf management applications, an implement can comprise a mower, sod cutter, sprayer, planter, etc.

In many agricultural operations, it is often desired to understand characteristics of the plant matter. For instance, site-specific farming refers to performing crop care functions, only where needed within a field. Therefore, some work has been done in sensing attributes of a field, plant matter within the field, and correlating them with geographic location, in order to generate maps or other geo-referenced data between the sensed attributes and their location within the field. Some systems sense attributes in a field by using images that are captured and processed to obtain plant matter data. This data can be utilized for controlling the agricultural operations, such as selecting a type and quantity of chemical to be sprayed on a particular plant based on a determination as to whether the plant is a weed or crop to be harvested.

The discussion above is merely provided for general background information and is not intended to be used as an aid in determining the scope of the claimed subject matter.

SUMMARY

An agricultural machine includes a vibration stimulation source configured to generate a vibration stimulation signal directed toward plant matter and a sensor system configured to sense electromagnetic radiation reflected from the plant matter, generate a first signal based on the sensed electromagnetic radiation, and generate a second signal indicative of a resonant vibration response of the plant matter, that is in response to the vibration stimulation signal. The agricultural machine includes a plant evaluation system configured to, based on the first and second signals, generate plant characterization data indicative of one or more physical characteristics of the plant matter, and a control system configured to generate an action signal based on the plant characterization data.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

The present disclosure generally relates to agricultural machines that process plant matter and more specifically, but not by limitation, to a plant evaluation and control architecture for an agricultural machine having resonance vibration response detection. The architecture performs plant matter evaluations based on the resonance vibration response detection, and generates corresponding control actions that can be utilized in a wide variety of agricultural operations. For example, plant matter evaluations can be utilized to control planting, crop care operations, and/or harvesting operations.

Before discussing detection, processing, and use of resonance vibration response in plant matter, it is noted that some approaches utilize plant image processing that rely on morphology (shape) or reflectance (color) analysis, which can be used in applications such as species (e.g., weed) identification, plant development staging, yield estimation, harvest date estimation, and/or health issue identification. Some such approaches can be inadequate due to factors such as similarities in reflectance signatures between crops and weeds, leaf damage, leaf occlusion, and/or characteristics which are not highly correlated with reflectance or shape. Further, images can be impacted by lighting, and still images only capture plant surface data. Thus, it can be difficult to distinguish between weeds and crops that have similar colors or leaf shapes, or where leaves have atypical shapes due to damage or occlusion by other plants.

Resonance imaging has been used in a lab setting, in which the plant leaves are well-defined and of a known species. This approach does not extend well, if at all, to a field setting where the plant species is unknown and/or the plant leaves are atypical.

Figure 1:
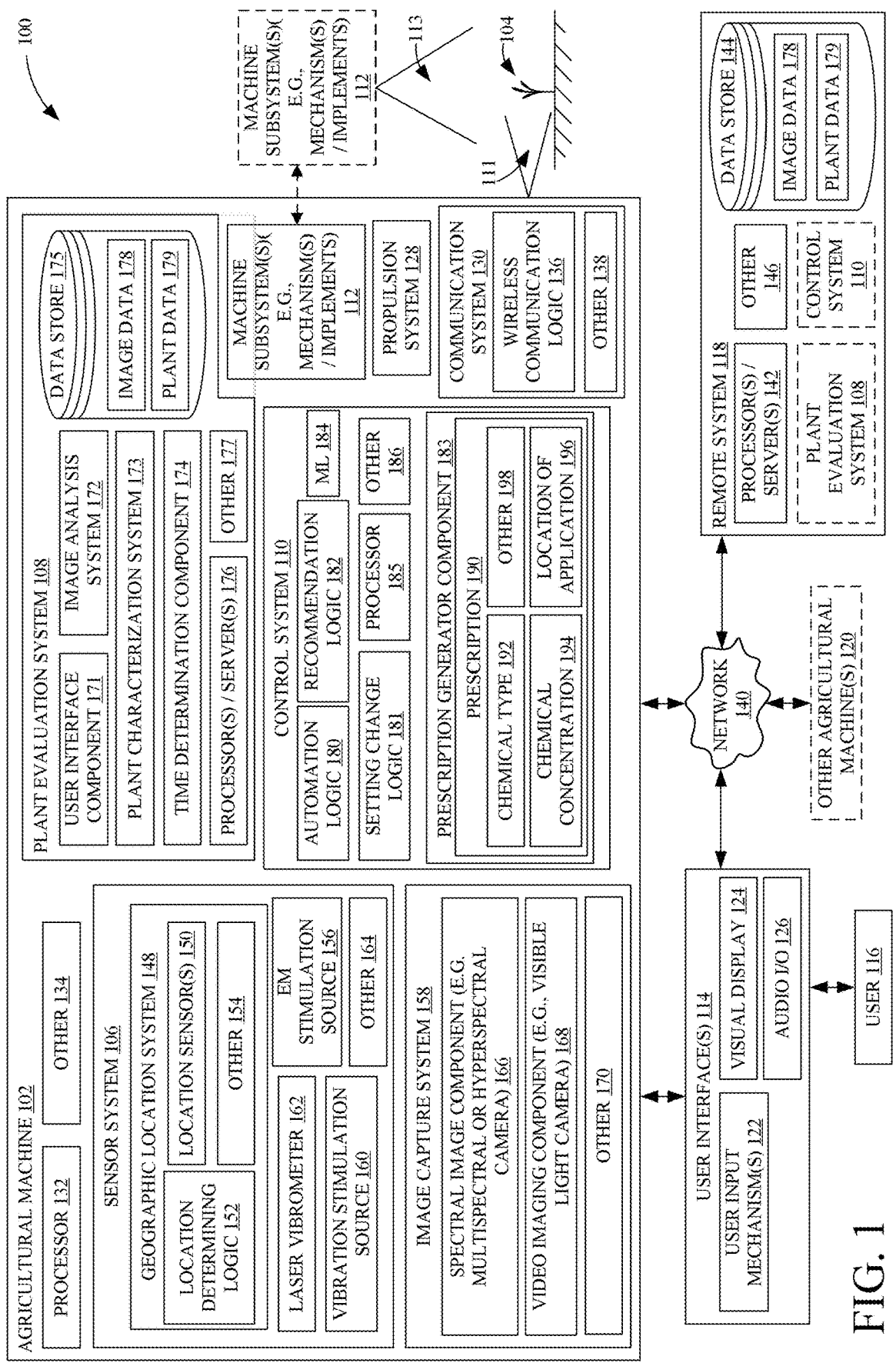
FIG. 1 is a block diagram of one example of an agricultural plant evaluation and control architecture.

FIG. 1 is a block diagram of one example of an agricultural plant evaluation and control architecture 100. Architecture 100 comprises an agricultural machine 102 configured to perform plant matter evaluations for plant matter generally represented by reference numeral 104 in FIG. 1. As discussed in further detail below, agricultural machine 102 is configured to perform plant shape and/or reflectance analysis, in combination with plant matter vibration analysis. This advantageously enhances plant matter evaluations and the resulting action control signals generated by or for an agricultural machine that is performing agricultural operations relative to the plant matter. For instance, accurate plant characterization and evaluation of the plant matter can improve spraying operations (or other agricultural operations such as reaping or harvesting) by precisely selecting the adequate chemical type and amount, as well as spraying locations, by being able to distinguish between weeds and the harvestable crop.

It is noted that while examples are described herein in the context of an agricultural machine performing crop care or other agricultural operation(s), the example systems, related components, and methods can be utilized in other types of machines and applications as well.

The term agricultural machine refers to a machine that is used in an agricultural process including, but not limited to, planting, spraying, harvest preparation, harvesting, as well as agricultural data collection and/or processing. For sake of illustration, an agricultural machine can include a seeder, a sprayer, a harvester, a swarm bot, or other agricultural implement configured to perform an agricultural operation. Further, an agricultural machine can include a support vehicle that tows, carries, pushes, or otherwise supports another agricultural machine, such as an implement or tool. One particular example includes a tractor that is driven by an operator and tows a sprayer implement.

Further, in one example an agricultural machine comprises an unmanned vehicle or drone (e.g., autonomous, semi-autonomous, and/or manually controlled) that operates in conjunction with an agricultural implement configured to perform an agricultural operation. For example, an unmanned aerial vehicle (UAV) can survey a portion of a field to acquire plant evaluation data prior to the agricultural implement operating in that portion of the field. For instance, the UAV can make passes through the field prior to (e.g., in front of) the agricultural implement operating in the field.

Further yet, in one example an agricultural machine comprises a handheld device, such as a mobile phone or other mobile device, that is carried by an operator to acquire plant evaluation data.

Agricultural machine 102 illustratively includes a sensor system 106 comprising one or more sensors configured to sense plant matter 104 (or other parameters relevant to machine 102) to generate corresponding signals/data that are provided to a plant evaluation system 108 and/or control system 110. Sensing plant matter is generally represented by reference numeral 111. Examples include, but are not limited to, sensing attributes such as crop type, weed presence, weed type, plant size, plant height, plant health, plant vigor, harvestable grain or fruit, etc. The sensors can be a wide variety of different types of sensors, such as cameras, infrared cameras or other infrared sensors, video cameras, stereo cameras, LIDAR sensors, structured light systems, etc.

Based on the output from sensor system 106, plant evaluation system 108 performs plant evaluation on plant matter 104 to generate a plant characterization signal (data) that is provided to control system 110, that generates an action signal based on the plant characterization data. Examples are discussed in further detail below. Briefly, however, the action signal can be sent by control system 110 to control a machine subsystem of agricultural machine 102, such as one or more machine subsystems (e.g., mechanism(s)/implement(s)) 112.

Example control can include adjusting an angle, chemical application type or rate, or pattern of a spray (generally represented by reference numeral 113). Other example control can include adjusting frame or ground-engaging element height above ground, ground-engaging element depth into or below ground, down pressure, or another mechanism control. Further, machine speed can be controlled, by controlling propulsion system 128. In various other applications, control system 110 can control boom height, nozzle size, solution delivery systems (flow and pressure), depth control, downforce systems, surface finish of the soil (e.g., is it level and smooth), cutter height, residue distribution systems, auger positions, spout positions, vehicle traction control systems, vehicle and implement steering control, among others.

As shown in FIG. 1, a controllable subsystem (e.g., 112) can be carried on or otherwise supported by agricultural machine 102. It is noted that in another example illustrated by dashed lines in FIG. 1, the controllable subsystem (e.g., 112) can comprise a separate machine, that is towed by agricultural machine 102 (e.g., a tractor or other support vehicle that is operated by an operator).

Example mechanism(s)/implement(s) 112 can include self-propelled sprayers, towed sprayers, mechanical weeders, laser weed killers, fertilizer applicators, planting machines, harvesters, and a wide variety of other machines.

Again, it is noted that agricultural machine 102 can comprise a separate machine that is not performing or otherwise supporting the agricultural operation. In one example, machine 102 comprises an unmanned (ground or aerial) vehicle or drone that obtains plant characterization data for another agricultural machine performing operations in the field using the data). In another example, agricultural machine 102 comprises a mobile computing device, such as a hand-held device (e.g., smartphone, etc.) that is carried by a user to acquire plant matter data and perform plant evaluations. An application on the a device is be utilized to generate an ultrasonic stimulation signal, through the device's speaker, an attached speaker, or a separate portable speaker. The camera of the device captures images that are used for color, shape, and/or resonance analysis.

The action signal can control agricultural machine 102 (or another machine or system) to generate user interfaces 114 to provide indications of the plant evaluations to a user 116. In another example, the action signal can control agricultural machine 102 to provide the plant evaluation data to a remote system 118 (e.g., for storage and/or further evaluation/action) and/or to other agricultural machine(s) 120.

Before discussing operation of architecture 100 in further detail, systems and components of machine 102 will be discussed. Agricultural machine 102 is shown generating user interfaces 114 with user input mechanisms 122. User input mechanisms 122 can be utilized by user 116 to control and manipulate agricultural machine 102, such as by controlling and manipulating one or more of sensor system 106, plant evaluation system 108, control system 110, or any other system/components of agricultural machine 102. User input mechanisms 122 can be rendered via a visual display 124 and/or audio input/output mechanisms 126. It is noted that, in one example, user interfaces 114 are generated in an operator compartment of agricultural machine 102. For example, a wide variety of user interface components to be provided such as, but not limited to, levers, switches, wheels, joysticks, buttons, a steering wheel, pedals, etc. The mechanisms can also include microphones with speech recognition systems and natural language processing systems, to process speech inputs. User input mechanisms can also be actuated from a user interface display on visual display 124, and they can include icons, links, drop down menus, radio buttons, text boxes, etc.

Agricultural machine 102 includes a propulsion system for propelling or otherwise moving agricultural machine 102 over or relative to a terrain. Therefore, propulsion system 128 can be any propulsion system that is suitable to the particular machine. In a case of a tractor or other similar support machine, propulsion system 128 can comprise an engine with a transmission that drives ground-engaging mechanisms such as wheels, tracks, etc.

In an example where agricultural machine 102 comprises an aerial drone, propulsion system 128 can drive rotors that move the drone over a field, for example. Agricultural machine 102 also includes, in the illustrated example, a communication system 130, one or more processors 132, and can include other items 134 as well.

Communication system 130 includes wireless communication logic 136, and can include other items 138. Using wireless communication logic 136, communication system 130 facilitates communication over a network 140, which can be a wide variety of different types of networks, such as the Internet, or another wide area network, a variety of other wireless or wired networks, etc. Wireless communication logic 136 can be substantially any wireless communication system that can be used by the systems and components of machine 102 to communicate information to other items in architecture 100, such as remote system 118.

Remote system 118 can be a wide variety of different types of systems. For example, remote system 118 can be a remote server environment, remote computer system that may be used, for instance, by a farmer, a farm manager, etc. Further, it can be a remote computing system, such as a mobile device, remote network, or a wide variety of other remote systems. The remote system 118 includes one or more processors or servers 142, a data store 144, and can include other items 146 as well. As illustrated in FIG. 1, and discussed in further detail below, remote system 118 can include portions (or all) of the various components of the illustrated systems shown in FIG. 1. For instance, one or more of plant evaluation system 108 and control system 110 can reside in remote system 118.

In the example illustrated in FIG. 1, sensor system 106 includes a geographic location system 148 that includes one or more location sensors 150, location determining logic 152, and can include other items 154 as well. Location sensor(s) 150 can comprise, for example, a satellite navigation receiver that receives satellite information from a positioning satellite. Based on the signal, location determining logic 152 determines a geographic location of agricultural machine 102, which can be correlated to the data obtained/generated by machine 102. Sensor system 106 also includes sensors and other components to detect electromagnetic radiation reflected by plant matter 104 and to detect vibration of plant matter 104. In the illustrated example, sensor system 106 includes an electromagnetic (EM) stimulation source 156, such as a source of visible or non-visible (infrared) light. This electromagnetic radiation can be received by image capture system 158, discussed in further detail below.

Sensor system 106 also includes a vibration stimulation source 160 configured to generate and direct a vibration stimulation system toward plant matter 104. This vibration stimulation source can be in the form of source of a mechanical wave, such as an acoustic wave, or otherwise. In one example, an ultrasonic signal is generated by vibration stimulation source 160 and stimulates vibration of plant matter 104. The vibration of plant matter 104 can be detected in a variety of different ways. In one example, a laser doppler vibrometer 162 detects the natural frequency or resonance frequency in response to the stimulation of plant matter 104. Sensor system 106 can include other items 164 as well.

Image capture system 158 include a spectral imaging component 166, such as a multi-spectral or hyper-spectral camera. Alternatively, or in addition, a video imaging component 168, such as a visible light camera, can be provided. Image capture system 158 can include other items 170 as well.

Spectral imaging component 166 includes a camera that takes spectral images of plant matter 104 and/or other portions of a field under analysis. Video imaging component 168 can include a camera that captures images in the visible or thermal infrared range. For instance, it can be a visible light video camera with a wide angle lens, or a wide variety of other video imaging systems.

Plant evaluation system 108 includes a user interface component 171 configured to generate user interfaces, such as user interface(s) 114 noted above. Plant evaluation system 108 also includes an image analysis system 172, a plant characterization system 173, a time determination component 174, a data store 175, and/or one or more processors or servers 176, and can include other items 177 as well. Image analysis system 172 is configured to receive image data from image capture system 158, and perform image analysis to obtain image data that is provided to plant characterization system 173, to perform plant matter evaluations to obtain plant characterization data. This is discussed in further detail below.

Time determination component 174 is configured to determine time information, for example to timestamp the image data 178 and/or plant data 179, which can be stored in data store 175. Alternatively, or in addition, image data 178 and/or plant data 179 can be stored in data store 144 of remote system 118. Image data 178 can include a priori response data indicative of known structure or conditions of a particular plant species, as well as in situ data that is captured and can be correlated with the a priori response information to generate the plant evaluations.

Control system 110 includes components/logic for generating action signals based on the plant characterization data, generated by plant evaluation system 108. Control system 110 includes automation logic for automating processes of machine 102, setting change logic 181 for changing settings of machine 102, recommendation logic 182 for generating action recommendations, a prescription generator component 183, a machine learning component 184, and/or one or more processors 185, and can include other items 186 as well.

Prescription generator component 183 is configured to generate a prescription 190 that can be consumed or otherwise utilized by automation logic 180, setting change logic 181, and/or recommendation logic 182. For example, but not by limitation, prescription 190 can indicate a type of chemical 192 to be applied to plant matter 104, a chemical concentration 194 to be applied to plant matter 104, a location 196 of the application, or other parameters 198 for the prescription. The prescription 190 can be rendered by recommendation logic 182 as a recommendation to user 116 through user interface(s) 114. In another example, the prescription 190 can be automatically implemented by automation logic 180, by changing settings of machine 102 using setting change logic 181. For example, this can include automatically controlling spray nozzles, pumps, or other components to apply the chemical type at the chemical concentration to the appropriate location in the field that corresponds to the plant matter 104. Alternatively, a harvester actuator, granular product meter, or liquid product meter can be controlled by control system 110. The prescription can prescribe chemicals that include pesticides, insecticides, fungicides, nematicides, etc. In another example, the chemicals can comprise nutrients such as nitrogen, phosphorus, potassium, micro-nutrients, among a wide variety of other chemicals.

Prescription 190 can be stored as geo-referenced data in data store 175, or another data store, for future use by machine 102 or another agricultural machine 120.

Figure 2:
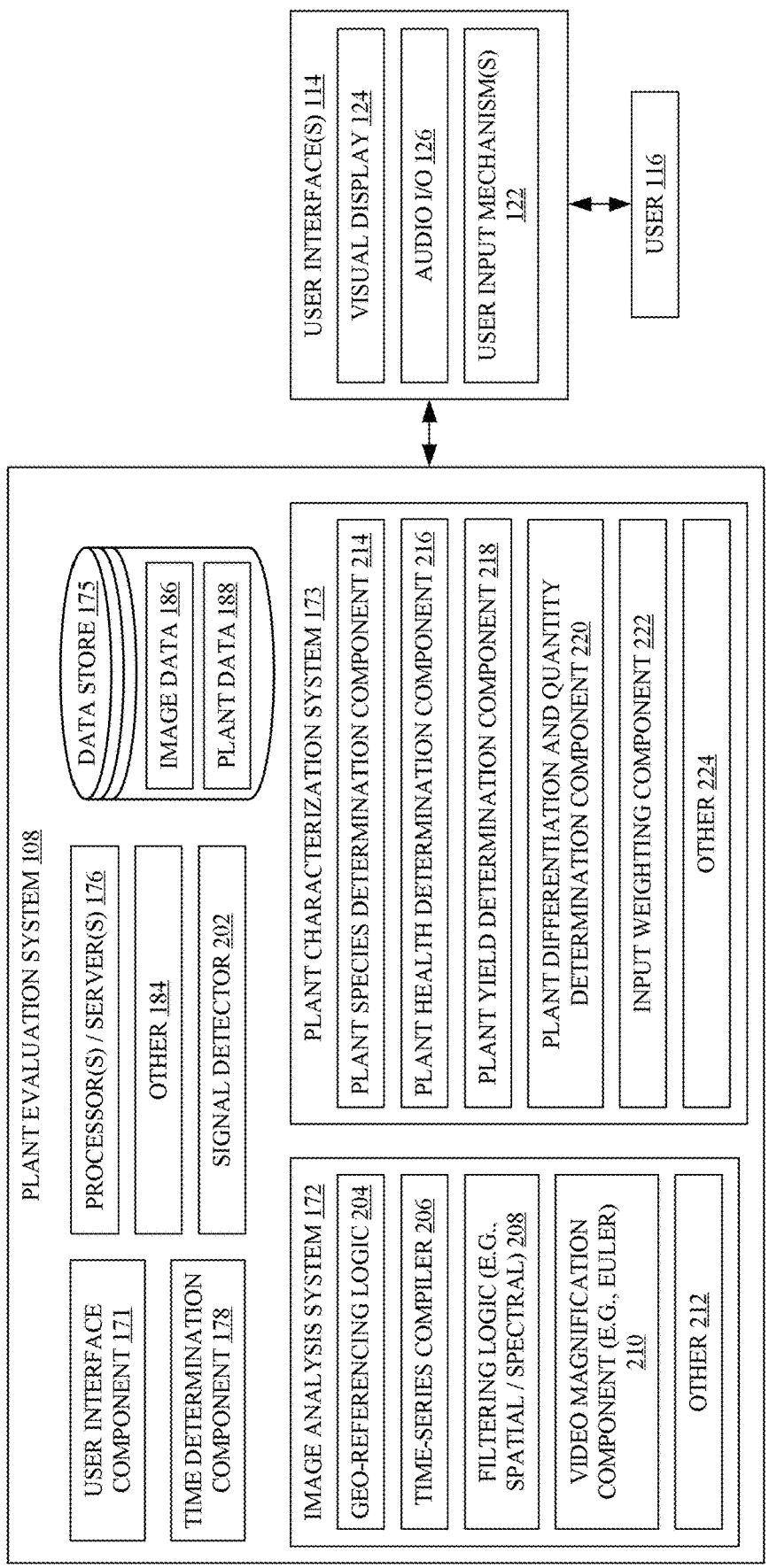
FIG. 2 is a block diagram of one example of a plant evaluation system.

FIG. 2 is a more detailed illustration of plant evaluation system 108, shown in FIG. 1. Plant evaluation system 108 illustratively includes a signal detector 202, configured to detect signals generated by sensor system 106. This includes, in the example illustrated above, a first signal that is based on sensed electromagnetic radiation reflected from plant matter 104 and a second signal indicative of a vibration response of plant matter 104, that is in response to a vibration stimulation signal. In the illustrated example, these signals include, or otherwise represent, image(s) captured by image capture system 158. These image(s) are analyzed by image analysis system 172, which includes geo-referencing logic 204, a time-series compiler 206, filtering logic 208, and/or a video magnification component 210. Image analysis system 172 can include other items 212 as well.

Geo-referencing logic 204 is configured to geo-reference the images received from image capture system 158 and/or the corresponding results of the image analysis, based on location information from geographic location system 148, which can be detected by signal detector 202. This geo-referenced image data can be stored as image data 178 in data store 175.

Time-series compiler 206 is illustratively configured to generate a time-series of images, which can construct a video sequence from a number of images captured by image capture system 158. Filtering logic 208 can be configured to perform special and/or spectral filtering of the image data. Video magnification component 210 includes, in one example, Eulerian video magnification that receives a video input and generates a magnified video output. Eulerian video magnification illustratively allows for very small changes in pixels to be magnified for further processing. In one example, motion vectors are utilized to process the video at real-time, or near real-time speeds.

In one example, filtering logic 208 is configured to perform digital image stabilization from the images. In one example, machine vibration caused by operation of agricultural machine 102 (e.g., based on moving components of propulsion system 128 or otherwise) is known or can be estimated. For instance, the machine vibration is at a known frequency that is a factor (e.g., multiple) of the engine speed, and can be filtered out by filtering logic 208.

In another example, the machine vibration can be eliminated or mitigated using vibration isolation, such as through hardware components, and/or software processing. For instance, the cameras of image capture system 158 can include integrated image stabilization features.

As shown in FIG. 2, plant characterization system 173 includes a plant species determination component 214, a plant health determination component 216, a plant yield determination component 218, plant differentiation and quantity determination component 220, and/or input weighting component 222, and can include other items 224 as well. Operation of these components is discussed in further detail below.

Briefly, however, plant species determination component (or logic) 214 is configured to determine a species of the plant matter 104 based on the signals generated from sensor system 106, that is indicative of sensed electromagnetic radiation (e.g., image(s)) reflected from the plant matter and a vibration response of the plant matter, that is response to the vibration stimulation signal generated by vibration stimulation source 160 (such as an ultrasonic signal). As noted above, weeds can be difficult to distinguish from crops because of similarity of light reflectance spectra or difficulty on discerning and classifying leaf shape due to occlusion or irregularities caused by such things as insect damage, soil on the leaf, angle of the leaf relative to the machine sensor(s). The resonant response, either in magnitude or gradient, provides another dimension for distinguishing plants from one another. The resonant response can be combined with size information to, for example, estimate the yield of an ear of corn, a soybean pod, or a head of small grain, etc.

Figure 3A:
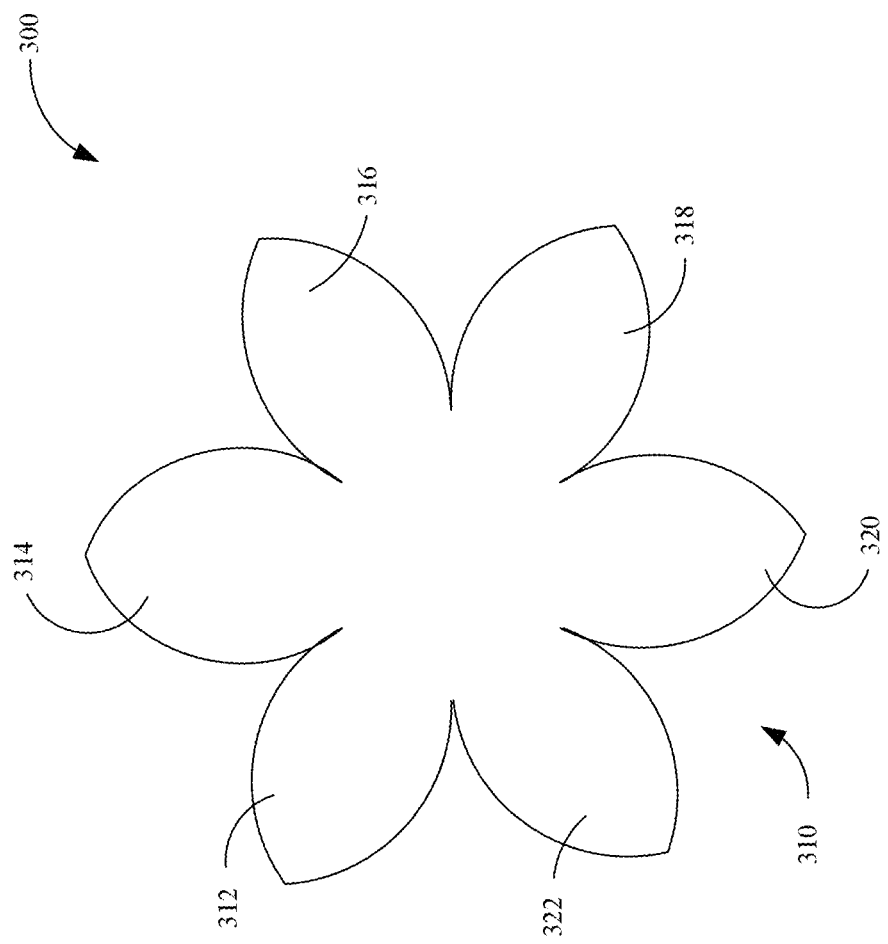
FIGS. 3A and 3B illustrate example images of plant matter.

For sake of illustration, FIG. 3A illustrates one example of a raw image 300 of a plant 310. Plant 310 appears to have six leaf lobes, labeled 312, 314, 316, 318, 320, and 322. However, in reality, plant 310 has three upper lobes and three lower lobes (e.g., a young soybean plant).

Figure 3B:
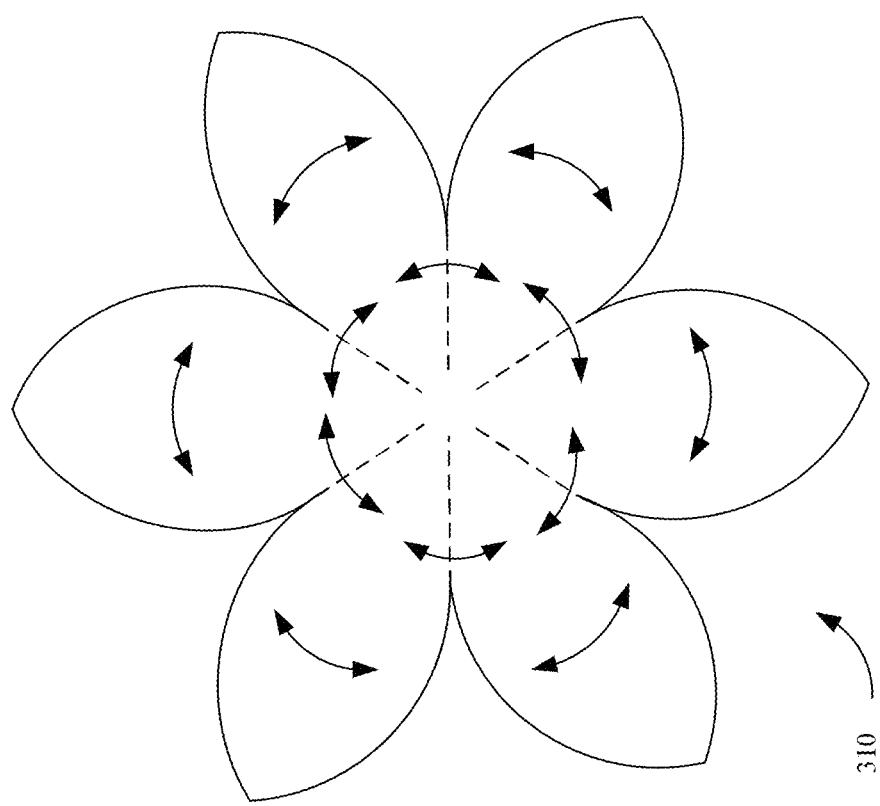

FIG. 3B illustrates one example of use of Eulerian video magnification and ultrasonic stimulation that facilitates improved distinction between lobes 312-322. As shown in FIG. 3B, the arrows represent the direction of vibration of various portions of plant 310. Boundaries between the upper and lower leaves are detected based on vibration amplitude, vibration frequency, vibration phase, or any other response which differs or otherwise distinguished between the leaves due to differences in response to vibration stimulation. In other words, detection of the vibrations represented by the arrows in FIG. 3B allow the boundaries of each leaf to be accurately distinguished, as well as to determine the lobes relative to position to one another (i.e., that there are three upper lobes and three lower lobes, as opposed to two separate three-lobed plants). Further, the gradient of the response (e.g., vibration magnitude or direction shift) can be used to distinguish discontinuities in a largely uniform color image. For example, a leaf boundary can be determined when one leaf occludes part of another.

Plant health determination component (or logic) 216 generates plant characterization data indicative of health characteristics of the plant matter. For instance, logic 216 can identify characteristics indicative of water stress as well as root rot, stem rot, and wilt attack. Further, discontinuities identified in the shape of the plant matter can be indicative of damage from insects or other causes. In one example, an image can be analyzed to determine absolute or relative height, diameter, or straightness of a plant, while the vibration response can indicate strength of the plant matter.

Further, in one example the resonance response is related to moisture content, and can be used to enhance color methods of tracking plant senescence and dry down. This enhanced data can be used for harvest planning such as field readiness, grain drying planning, harvest logistics planning, to estimate a harvest date.

Plant yield determination component (or logic) 218 provides an on-plant yield assessment from the sensed data. Per-plant yield measurement can be generated and used in a wide variety of ways. For instance, this information can be provided to remote system 118 to generate crop planning data that correlates planting operations and/or crop care operations (spraying, etc.) to the yield on a per-plant basis. The resonance response of the plant matter can be correlated to yield and used during harvesting operations, for example to generate control instructions for a harvesting machine.

The resonance response is, in one example, utilized to enhance the image analysis to obtain information concerning hidden or occluded the harvested plant material. For instance, the resonance response can be utilized to determine the volume of plant material inside an ear of corn, a peapod, etc. These plant parts are not otherwise observable, directly, from the image data. Further, during the vegetative stage. resonance response can give insight into the interior structure of the plants that can be impacted by such things as treatable stresses from water or disease issues.

Plant differentiation and quantity determination component (or logic) 220 can be configured to differentiate between separate plants, in a mass of plant matter imaged from a field. For example, it may not be possible to distinguish between two plants having similar color in an image. The resonance response from that plant matter can determine the boundaries of the plant parts, and thus utilize to determine that the image actually includes two or more separate plants.

Input weighting component 222 is configured to weight or otherwise combine the image and vibration response signals. For example, component 222 determines (through rules, lookup tables, or otherwise) how the image and vibration response data can be combined by components 214-220. For instance, component 222 can weight the image data more highly in a plant species determination by component 214, but less heavily in determining plant health or differentiation/quantity determination. These, of course, are examples only.

Figure 4:
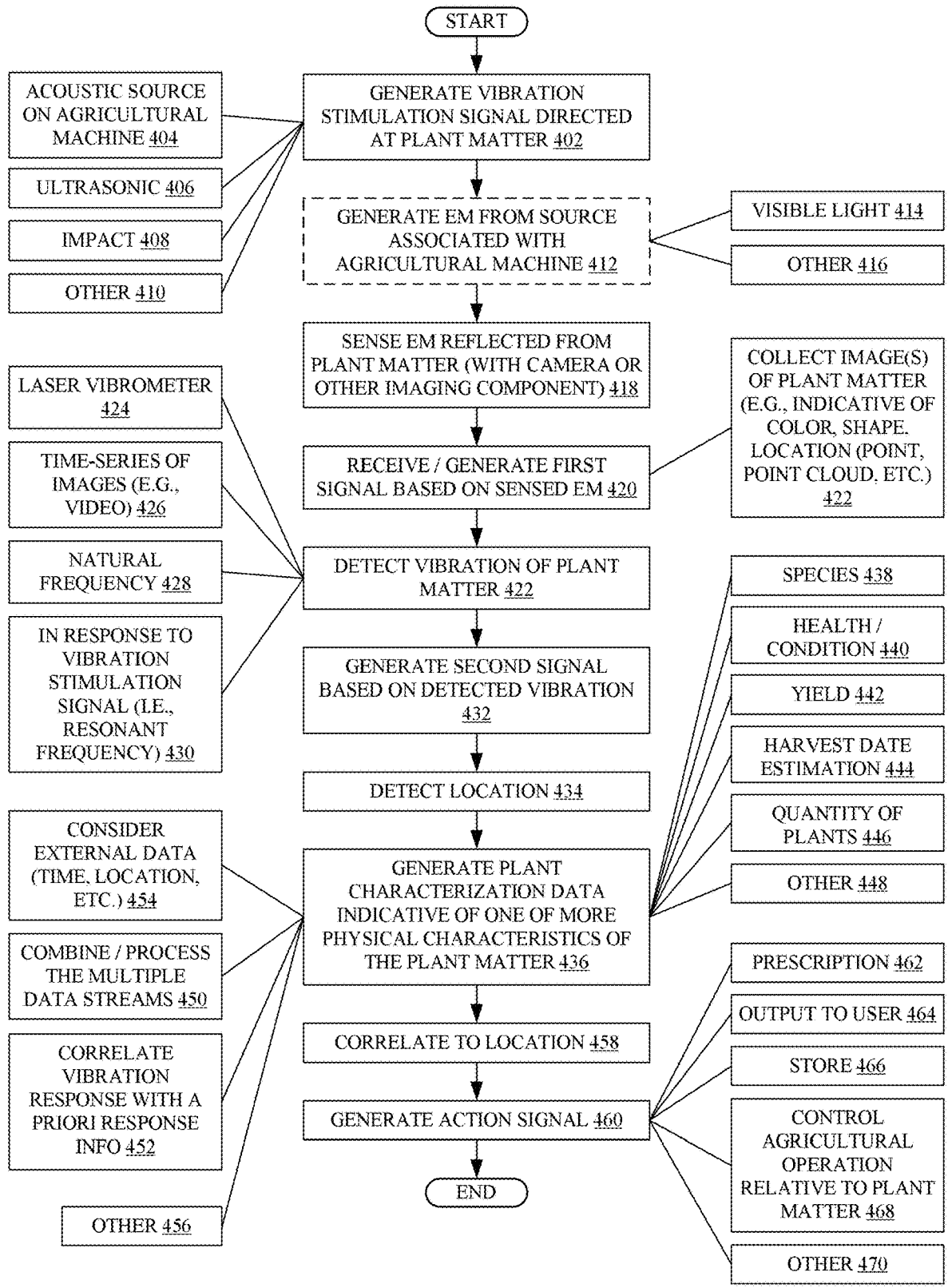
FIG. 4 is a flow diagram illustrating one example of a method for plant characterization and machine control.

FIG. 4 is a flow diagram illustrating one example of a method 400 of plant characterization and machine control. For sake of illustration, but not by limitation, method 400 will be described in the context of architecture 100 illustrated in FIG. 1.

At step 402, a vibration stimulation signal is generated and directed at plant matter 104. In the illustrated example, the vibration stimulation signal comprises a mechanical wave, such as, but not limited to, an acoustic wave generated by source 160. This is represented by block 404. The vibration stimulation signal can be ultrasonic, as represented by block 406. Alternatively, or in addition, the signal can comprise impact of the plant (represented by block 408), such as with an air pulse, or can be generated in other ways as well (represented by block 410).

In one example of method 400, electromagnetic radiation is generated (412) from a source associated with machine 102. For instance, visible (or invisible) light 414 is generated by source 156. The electromagnetic radiation can be generated in other ways as well. This is represented by 416. In other examples, ambient light such as sunlight is used in place of a source associated with a machine.

At block 418, the method senses electromagnetic radiation reflected from plant matter 104. In one example, this is done using a camera or other imaging component of image capture system 158. The electromagnetic radiation can be natural light and/or the electromagnetic radiation generated at block 412.

At block 420, a first signal is generated based on the sensed electromagnetic radiation, that is sent at block 418. For instance, the images can include or otherwise represent images of the plant matter collected at block 422. The images are indicative of color, shape, and/or location of parts of plant matter 104.

In one example, block 422 generates a point or point cloud representing the plant matter. A point cloud comprises a set of data points in space, and represent a number of points on external surfaces of the object. A three-dimensional profile or height map can be generated by projecting various structured light patterns from a source onto an object, and recording the patterns with one or more cameras, and processing the image(s). The point cloud is defined in a coordinate system, such as an x, y, z coordinate system.

At block 424, a vibration (e.g., vibration response) of the plant matter is detected. In one example, as noted above, this can be done using a laser vibrometer, such as laser vibrometer 162. This is represented at block 424. In another example, detection at block 422 can be performed using a time-series of images. This is represented by block 426. For instance, time-series compiler 206 can compile a number of individual images into a series of images. Alternatively, a video can be obtained in other ways as well. For instance, a video imaging component can be utilized.

The detected vibration, in one example, can be indicative of a natural frequency, which is a frequency at which a system tends or oscillate in the absence any driving or damping force. Natural frequencies differ from forced vibrations which happen at frequency of applied force, or forced frequency. If forced frequency is equal to the natural frequency 428, the amplitude of vibration increases. This is referred to as resonance.

As represented at block 430, the response to the vibration stimulation signal is detected (i.e., the resonant frequency). As noted above, resonance is the phenomenon in which a vibrating system or external force drives another system to oscillate with greater magnitudes at specific frequencies. Frequencies at which the response amplitude is a relative maximum are referred to as relative frequencies or resonance frequencies.

At block 432, a second signal is generated based on the detected vibration. The second signal represents the vibration of one or more areas of the plant matter (such as the arrows in FIG. 3B).

At block 434, location is detected, for example using geographic location system 148. This detected location is indicative of a location of plant matter 104, for which the first and second signals are generated.

At block 436, plant characterization data is generated, and is indicative of one or more physical characteristics of the plant matter. For instance, as noted above, the physical characteristics can comprise one or more of a plant species 438, plant health or condition 440, yield 442, harvest day estimation 444, a quantity of plants 446, and can include other characteristics 448. This can be done in a number of ways. For instance, the data can be compared to a priori information. Look-up tables (or other data structures) can be used to compare/map the morphology, shape, and/or vibration response information (or any other sensed attributes) from plant matter 104 to known or otherwise predefined plant characteristics. This can be based on one or more of prior data obtained from the same plant matter 104, prior data obtained by machine 102, prior data obtained by other machine(s) 120, data from remote system 118, or any other data that correlates sensed attributes to plant characteristics.

Generation of plant characterization data is illustratively performed by combining/processing the multiple data streams at block 450. For example, but not by limitation, the morphology (shape) and color information can be used to identify a species of plant matter 104 and the vibration response can be correlated with a priori response information (at block 452), to assess the structure of condition of the plant. The correlation can be improved with absolute or relative size from an image or with color from the image collected at block 422.

For instance, in one example of block 440, plant health is assessed by analyzing the frequency of a leaf of plant matter 104, which is proportional to the rigidity or stiffness of the leaf. This can further be utilized to obtain an indication of water pressure in the leaf. Detection of pressure or water content below an expected level can be indicative of root rot, stem rot, or wilt attack.

In another example of block 438, color information from block 420 is utilized to identify a set of possible plant species, that have the same or similar color. Then, the vibration response information is utilized to distinguish between separate plant parts, such as by determining that a mass of plant matter in the capture image is actually separate leaf lobes on a same plant or different plants. This information is then utilized to select the appropriate species from the set (based on expected vibration responses of each species pre-defined thresholds, or otherwise) and/or determine how many plants of that species are in the image (block 446).

In another example of block 442, the resonant response can be combined with size information to estimate yield of a corn ear, soybean pod, or head of small grain. The resonant response can provide information about the mass of plant matter that is hidden or occluded in the image (such as the volume inside an ear of corn, a peapod, etc.). The mass estimate may be in absolute terms such as grams or in relative terms between plants such as "similar", "x is more than y", or "x is much larger than y".

Additionally, in the correlation process, external data can be considered at block 454, and used in correlating the vibration response to the a priori response information. For instance, the external data can indicate a time and/or location that corresponds to the detected signals. Thus, if the data is acquired early in the day, it may expected that the moisture content of a particular plant species will be higher than if the data is obtained later in the day. Further, based on the on-plant yield assessment, time information can be utilized to estimate a harvest date.

Of course, the signals can be correlated, combined, or weighted in other ways as well. This is represented by block 456.

At block 458, the plant characterization data is correlated to the location detected at block 434. This is utilized to generate an action signal at block 460. For instance, the action signal can comprise a prescription 190 generated by prescription generator component 183. Examples of this are discussed above. This is represented at block 462. In another example, the action signal can control user interface components to output the prescription, a recommended action, and/or the plant characterization data itself, to user 116. This is represented at block 464.

Further, the action signal can instruct a data store to store the geo-referenced plant characterization data. This is represented at block 466. For instance, the data can be stored in data store 175 and/or data store 144.

Further, the action signal can control an agricultural operation relative to the plant matter. This is represented by block 468. In one example, application of agricultural inputs and/or adjustment of machine actuators is controlled by control system 110. In one example, this can be performed using machine learning component 184. Alternatively, or in addition, the selection of substances and amounts, plant measurements, actuator adjustments, can include rule-based logic, lookup tables, and/or mathematical formulas that are stored in or otherwise retrieved by machine 102.

Figure 5:
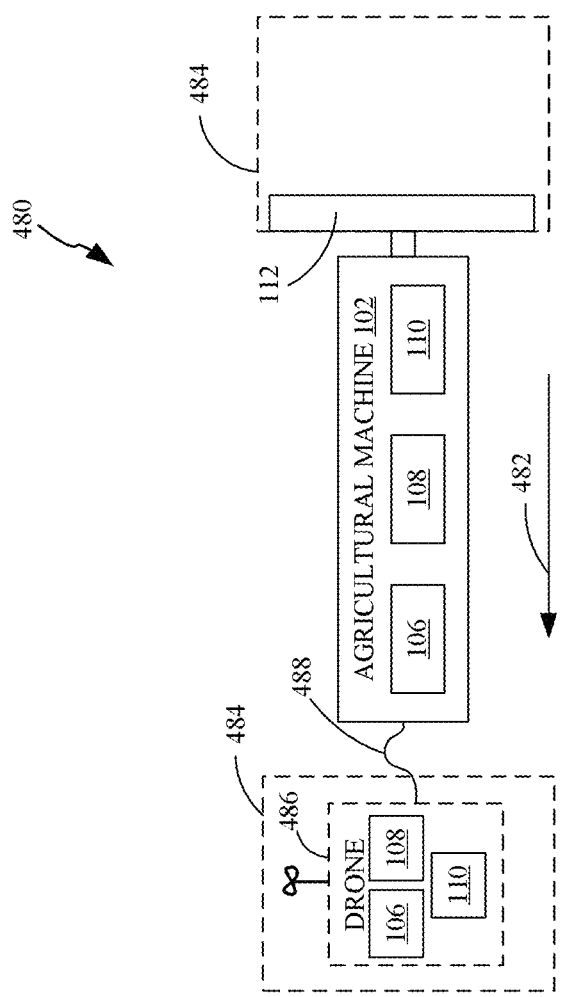
FIG. 5 is a schematic diagram illustrating an example application of the architecture illustrated in FIG. 1.

FIG. 5 is a schematic diagram 480 illustrating one application of architecture 100. As shown in FIG. 5, agricultural machine 102 is propelled in a direction 482 across a field having an area 484 of plant matter. Using sensor system 106, agricultural machine 102 captures images and vibration information from the plant matter in area 484, which is provided to plant evaluation system 108, which generates plant characterization data that is used by control system 110 in generating and implementing a control action. For example, the control action can control agricultural implement 112, such as a sprayer that sprays an herbicide or other chemical, when it passes over area 484.

In another example, one or more of systems 106, 108, and 110 can be provided on a separate agricultural machine, such as, but not limited to, a drone 486. As drone 486 passes over area 484, ahead of agricultural machine 102, it captures images, detects vibration, and/or evaluates plant characterization data from area 484. Using control system 110, which can be on drone 486, or agricultural machine 102 (or components of system 110 can be distributed between drone 486 and machine 102), agricultural implement 112 can be controlled. For instance, this can be done through a wired or wireless link 488.

It can thus be seen that the present system provides a number of advantages. For example, the present system enhances plant matter evaluation through supplementation of plant shape and/or color data acquired through image processing, with vibration stimulation and detection. A light pattern can overgo multiple reflections from the plant matter before it is imaged by the camera(s). These reflections can cause severe errors, or noise, in the point cloud that is created based on the images. Multiple reflections can be worsened by shiny or a specular object. Further, if there is overlap in the plant matter, portions of the plant matter can be obscured. Use of vibration response detection can mitigate, if not eliminate, these issues.

Vibration response detection can be utilized for identification of a number of characteristics, such as species identification, yield estimation, plant health determination, harvest time estimation, and/or to distinguish between separate plants. For sake of illustration, an agricultural machine may pass through a field having a number of plants that include both weeds and crop to be operated upon. However, from an imaging sensor output, the plant material may appear as a large mass of plant matter, with little or no ability to distinguish between separate plants (e.g., two or more adjacent plants may blend together and appear to be one large plant matter mass). By processing sensed vibration characteristics of the plant matter, the system can determine that the plant mass consists of multiple, separate plants, and/or can distinguish between plants of different species when the plants have similar color, shape, or other physical characteristics. This improves the agricultural machine and process itself, by improving the precision of the control system, in generating the control actions used to control the agricultural machine or other machine in the agricultural process.

It will be noted that the above discussion has described a variety of different systems, components and/or logic. It will be appreciated that such systems, components and/or logic can be comprised of hardware items (such as processors and associated memory, or other processing components, some of which are described below) that perform the functions associated with those systems, components and/or logic. In addition, the systems, components and/or logic can be comprised of software that is loaded into a memory and is subsequently executed by a processor or server, or other computing component, as described below. The systems, components and/or logic can also be comprised of different combinations of hardware, software, firmware, etc., some examples of which are described below. These are only some examples of different structures that can be used to form the systems, components and/or logic described above. Other structures can be used as well.

The present discussion has mentioned processors and servers. In one example, the processors and servers include computer processors with associated memory and timing circuitry, not separately shown. They are functional parts of the systems or devices to which they belong and are activated by, and facilitate the functionality of the other components or items in those systems.

Also, a number of user interface displays have been discussed. They can take a wide variety of different forms and can have a wide variety of different user actuatable input mechanisms disposed thereon. For instance, the user actuatable input mechanisms can be text boxes, check boxes, icons, links, drop-down menus, search boxes, etc. They can also be actuated in a wide variety of different ways. For instance, they can be actuated using a point and click device (such as a track ball or mouse). They can be actuated using hardware buttons, switches, a joystick or keyboard, thumb switches or thumb pads, etc. They can also be actuated using a virtual keyboard or other virtual actuators. In addition, where the screen on which they are displayed is a touch sensitive screen, they can be actuated using touch gestures. Also, where the device that displays them has speech recognition components, they can be actuated using speech commands.

A number of data stores have also been discussed. It will be noted they can each be broken into multiple data stores. All can be local to the systems accessing them, all can be remote, or some can be local while others are remote. All of these configurations are contemplated herein.

Also, the figures show a number of blocks with functionality ascribed to each block. It will be noted that fewer blocks can be used so the functionality is performed by fewer components. Also, more blocks can be used with the functionality distributed among more components.

Figure 6:
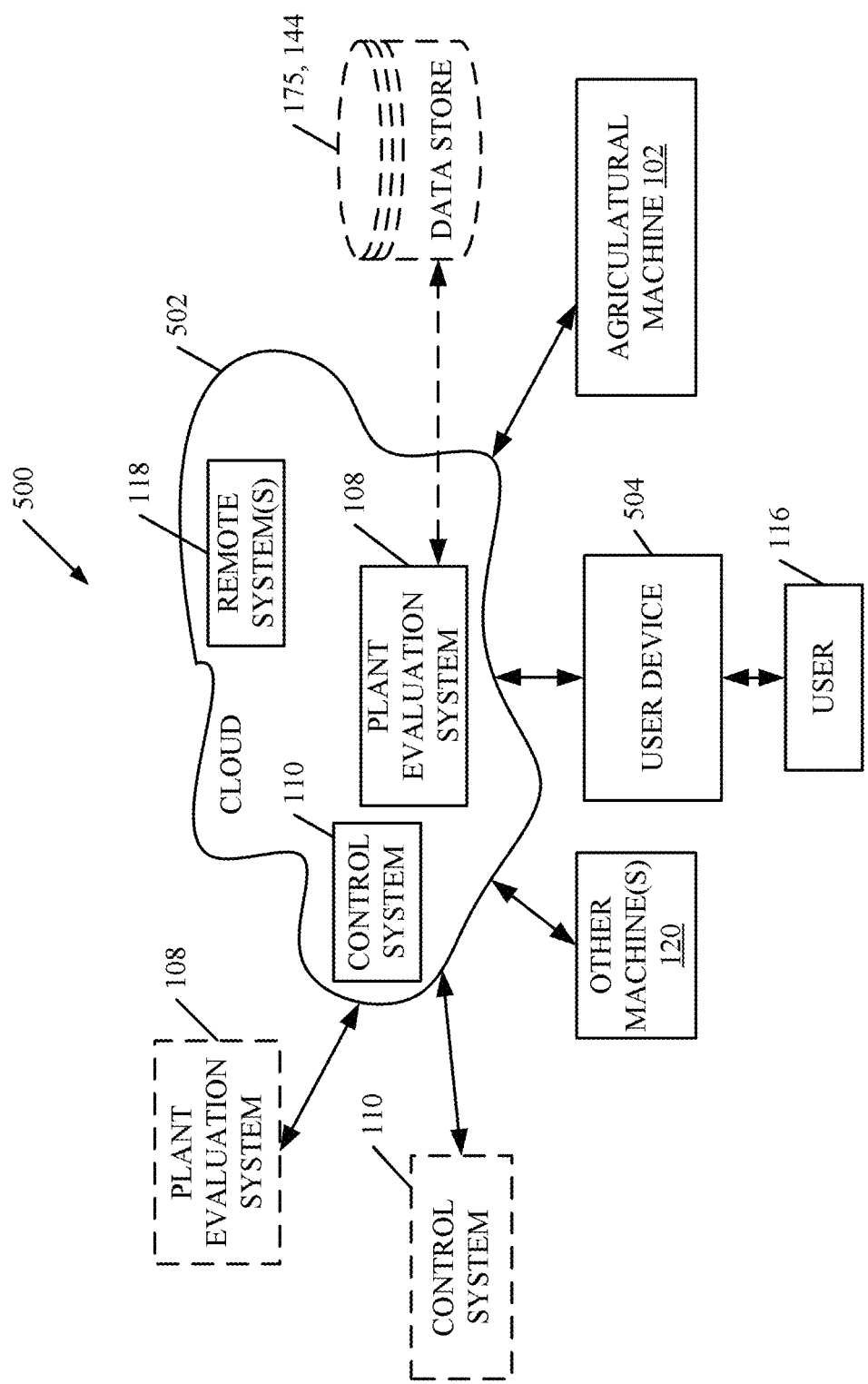
FIG. 6 is a block diagram of one example of the architecture illustrated in FIG. 1, deployed in a remote server architecture.

FIG. 6 is a block diagram of architecture 100, shown in FIG. 1, except that it is deployed in a remote server architecture 500. In an example, remote server architecture 500 can provide computation, software, data access, and storage services that do not require end-user knowledge of the physical location or configuration of the system that delivers the services. In various embodiments, remote servers can deliver the services over a wide area network, such as the internet, using appropriate protocols. For instance, remote servers can deliver applications over a wide area network and they can be accessed through a web browser or any other computing component. Software or components shown in FIG. 1 as well as the corresponding data, can be stored on servers at a remote location. The computing resources in a remote server environment can be consolidated at a remote data center location or they can be dispersed. Remote server infrastructures can deliver services through shared data centers, even though they appear as a single point of access for the user. Thus, the components and functions described herein can be provided from a remote server at a remote location using a remote server architecture. Alternatively, they can be provided from a conventional server, or they can be installed on client devices directly, or in other ways.

In the example shown in FIG. 6, some items are similar to those shown in FIG. 1 and they are similarly numbered. FIG. 6 specifically shows that remote system 118, plant evaluation system 108, control system 110 can be located at a remote server location 502. The information can be provided to remote server location 502 by machine 102 (e.g., from sensor system 106) in any of a wide variety of different ways. Therefore, user 116 and/or machines 102 and 120 can access those systems through remote server location 502. This can be done using a user device 504, for instance.

FIG. 6 also depicts another embodiment of a remote server architecture. FIG. 6 shows that it is also contemplated that some elements of FIG. 1 are disposed at remote server location 502 while others are not. By way of example, data stores 144 and/or 175 can be disposed at a location separate from location 502, and accessed through the remote server at location 502. In another example, plant evaluation system 108 can be disposed at a location separate from location 502, and accessed through the remote server at location 502. In another example, control system 110 can be disposed at a location separate from location 502, and accessed through the remote server at location 502. Regardless of where they are located, they can be accessed directly by user device 506, through a network (either a wide area network or a local area network), they can be hosted at a remote site by a service, or they can be provided as a service, or accessed by a connection service that resides in a remote location. Also, the data can be stored in substantially any location and intermittently accessed by, or forwarded to, interested parties. For instance, physical carriers can be used instead of, or in addition to, electromagnetic wave carriers. In such an embodiment, where cell coverage is poor or nonexistent, another mobile machine (such as a fuel truck) can have an automated information collection system. As the machine comes close to the fuel truck for fueling, the system automatically collects the information from the harvester using any type of ad-hoc wireless connection. The collected information can then be forwarded to the main network as the fuel truck reaches a location where there is cellular coverage (or other wireless coverage). For instance, the fuel truck may enter a covered location when traveling to fuel other machines or when at a main fuel storage location. All of these architectures are contemplated herein. Further, the information can be stored on machine 102 until the machine enters a covered location. The machine, itself, can then send the information to the main network.

It will also be noted that the elements of FIG. 1, or portions of them, can be disposed on a wide variety of different devices. Some of those devices include servers, desktop computers, laptop computers, tablet computers, or other mobile devices, such as palm top computers, cell phones, smart phones, multimedia players, personal digital assistants, etc.

Figure 7:
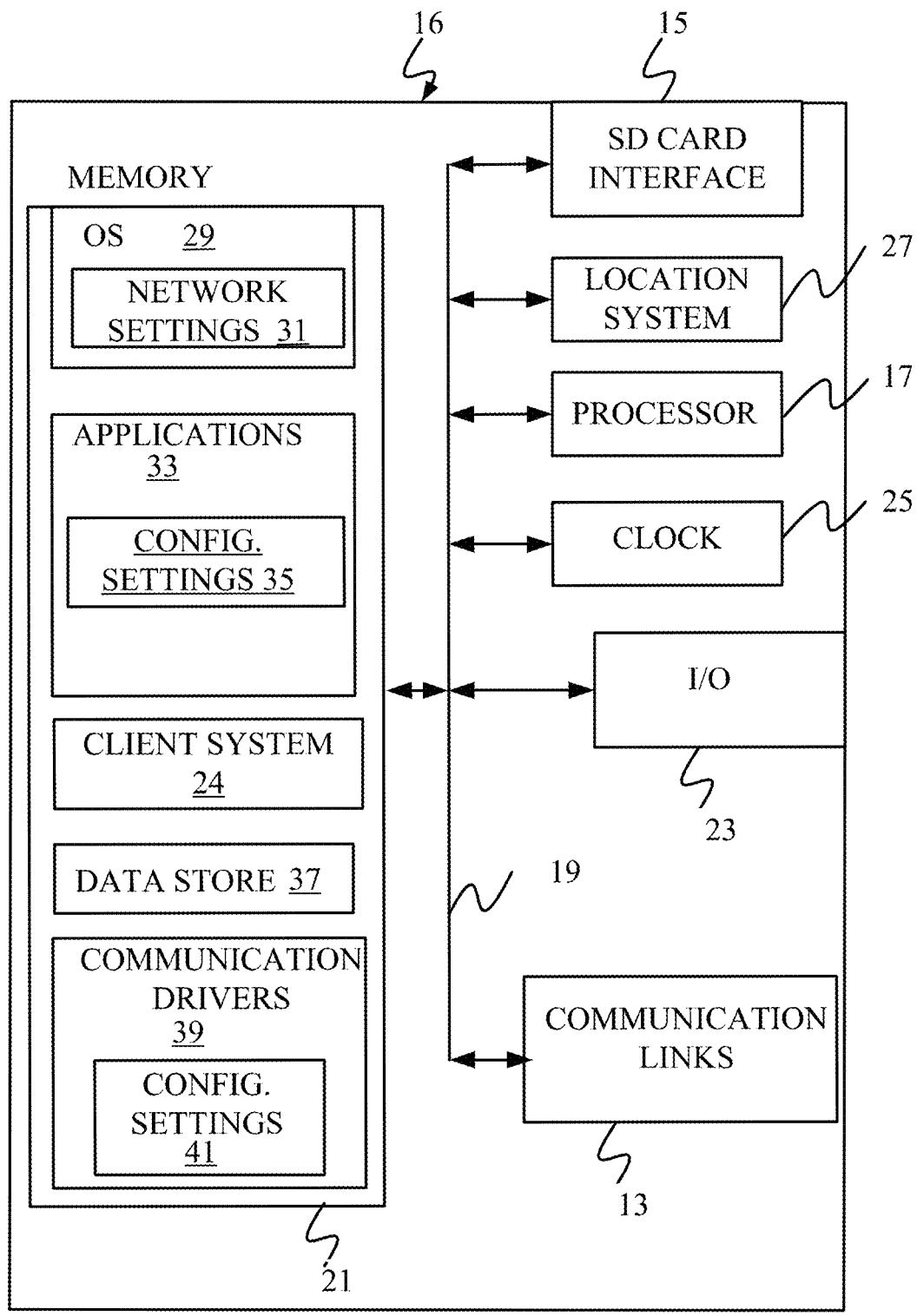
FIGS. 7-9 are examples of mobile devices that can be used in the architectures illustrated in the previous figures.
Figure 8:
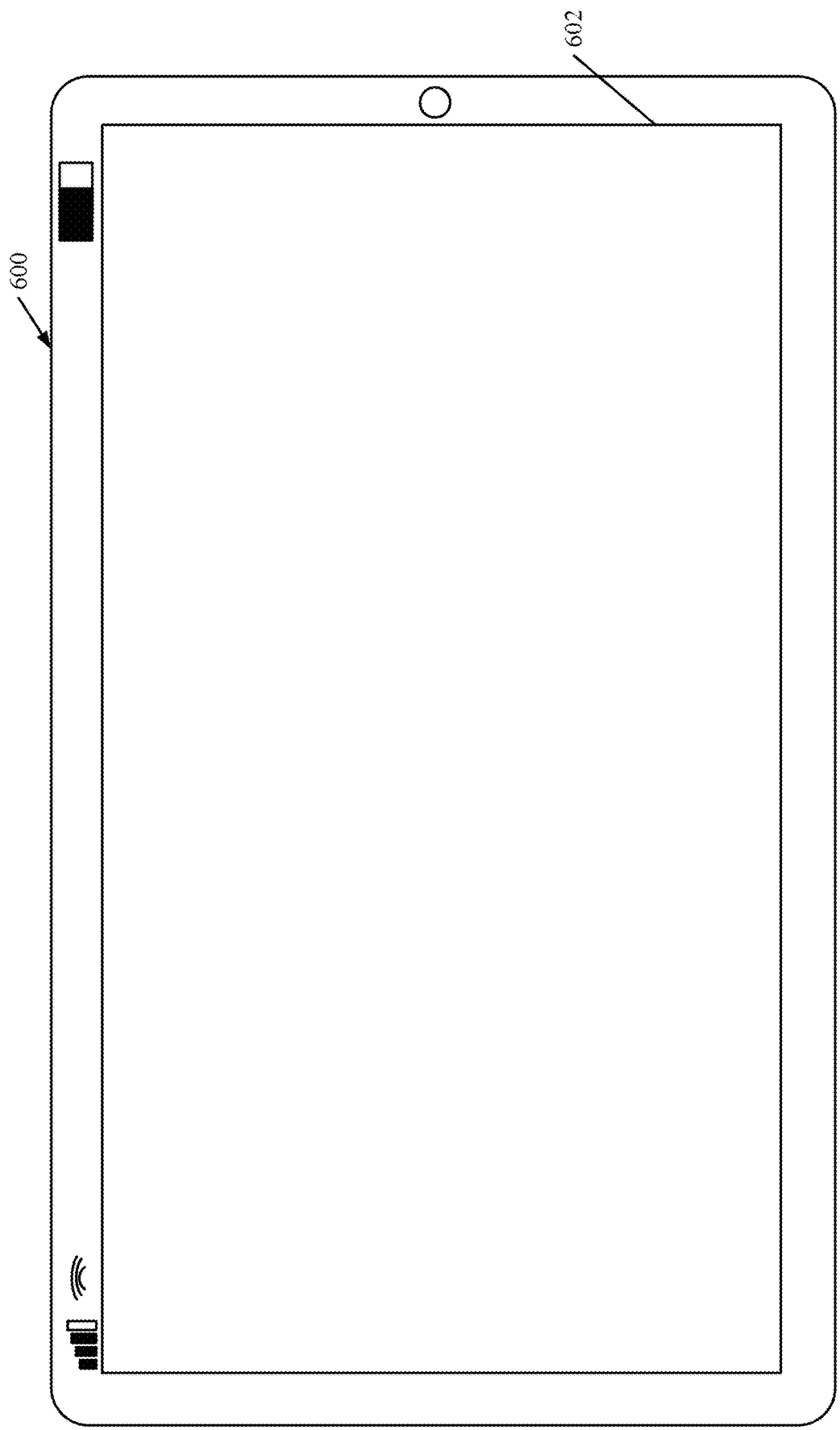
Figure 9:
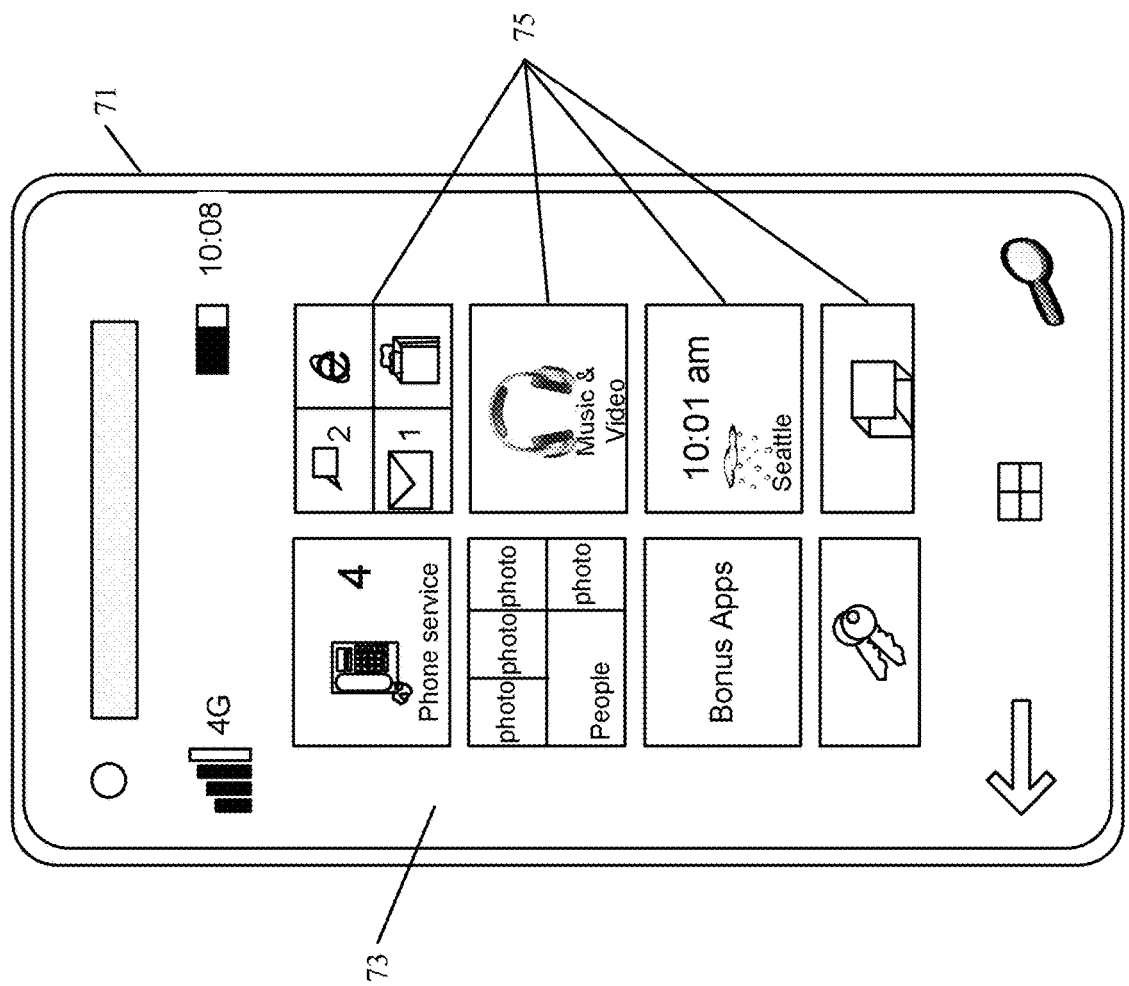

FIG. 7 is a simplified block diagram of one illustrative example of a handheld or mobile computing device that can be used as a user's or client's hand held device 16, in which the present system (or parts of it) can be deployed. For instance, a mobile device can be deployed in the operator compartment of machines 102 and 120, or as user device 504 for use in generating, processing, or displaying the plant evaluation information. FIGS. 8-9 are examples of handheld or mobile devices.

FIG. 7 provides a general block diagram of the components of a client device 16 that can run some components shown in FIG. 1, that interacts with them, or both. In the device 16, a communications link 13 is provided that allows the handheld device to communicate with other computing devices and under some embodiments provides a channel for receiving information automatically, such as by scanning. Examples of communications link 13 include allowing communication though one or more communication protocols, such as wireless services used to provide cellular access to a network, as well as protocols that provide local wireless connections to networks.

In other examples, applications can be received on a removable Secure Digital (SD) card that is connected to an interface 15. Interface 15 and communication links 13 communicate with a processor 17 (which can also embody any processor or server from previous Figures) along a bus 19 that is also connected to memory 21 and input/output (I/O) components 23, as well as clock 25 and location system 27.

I/O components 23, in one embodiment, are provided to facilitate input and output operations. I/O components 23 for various embodiments of the device 16 can include input components such as buttons, touch sensors, optical sensors, microphones, touch screens, proximity sensors, accelerometers, orientation sensors and output components such as a display device, a speaker, and or a printer port. Other I/O components 23 can be used as well.

Clock 25 illustratively comprises a real time clock component that outputs a time and date. It can also, illustratively, provide timing functions for processor 17.

Location system 27 illustratively includes a component that outputs a current geographical location of device 16. This can include, for instance, a global positioning system (GPS) receiver, a LORAN system, a dead reckoning system, a cellular triangulation system, or other positioning system. It can also include, for example, mapping software or navigation software that generates desired maps, navigation routes and other geographic functions.

Memory 21 stores operating system 29, network settings 31, applications 33, application configuration settings 35, data store 37, communication drivers 39, and communication configuration settings 41. Memory 21 can include all types of tangible volatile and non-volatile computer-readable memory devices. It can also include computer storage media (described below). Memory 21 stores computer readable instructions that, when executed by processor 17, cause the processor to perform computer-implemented steps or functions according to the instructions. Processor 17 can be activated by other components to facilitate their functionality as well.

FIG. 8 shows one embodiment in which device 16 is a tablet computer 600. In FIG. 8, computer 600 is shown with user interface display screen 602. Screen 602 can be a touch screen or a pen-enabled interface that receives inputs from a pen or stylus. It can also use an on-screen virtual keyboard. Of course, it might also be attached to a keyboard or other user input device through a suitable attachment mechanism, such as a wireless link or USB port, for instance. Computer 600 can also illustratively receive voice inputs as well.

FIG. 9 shows that the device can be a smart phone 71. Smart phone 71 has a touch sensitive display 73 that displays icons or tiles or other user input mechanisms 75. Mechanisms 75 can be used by a user to run applications, make calls, perform data transfer operations, etc. In general, smart phone 71 is built on a mobile operating system and offers more advanced computing capability and connectivity than a feature phone.

Note that other forms of the devices 16 are possible.

Figure 10:
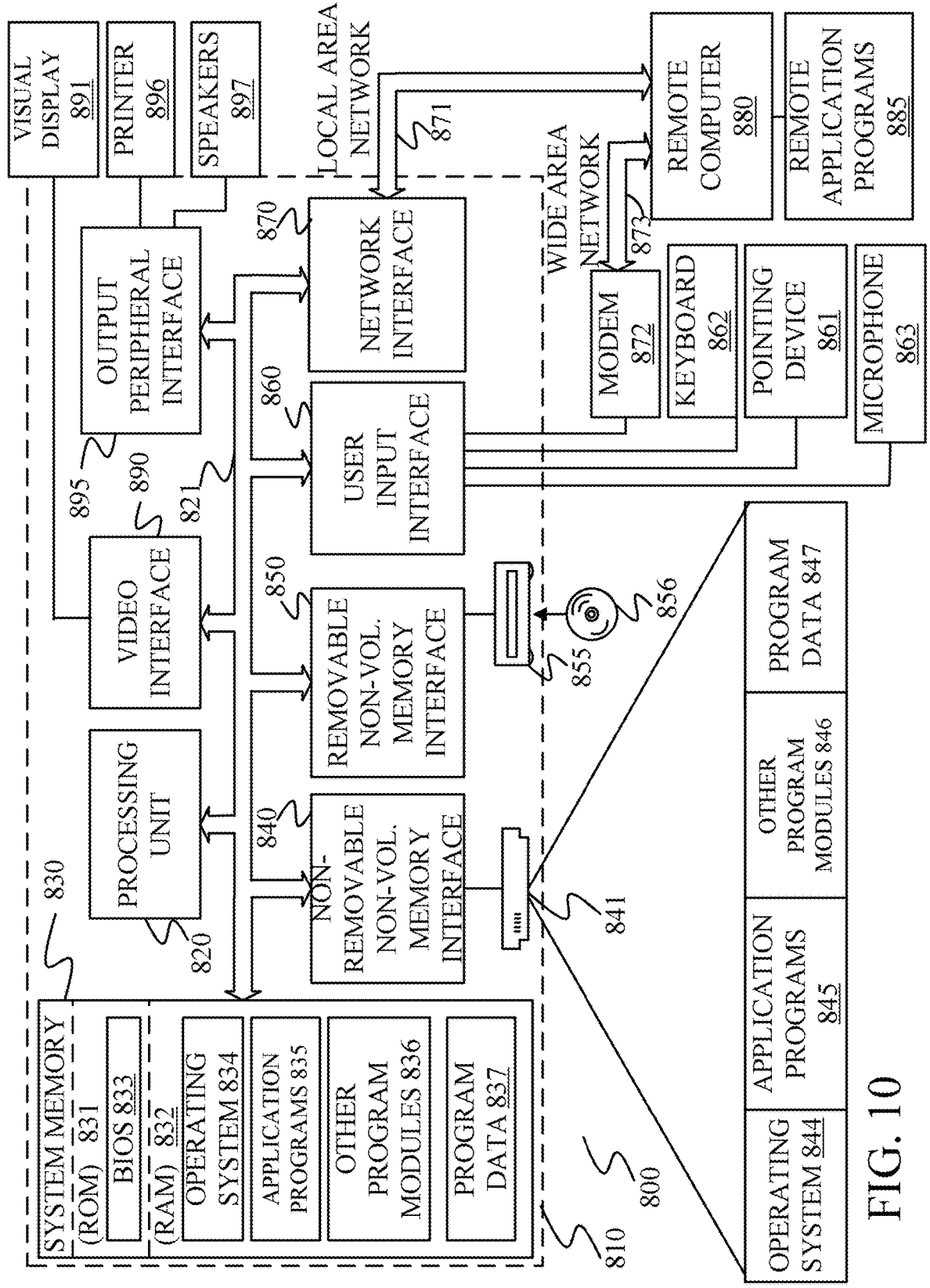
FIG. 10 is a block diagram of one example of a computing environment that can be used in the architectures shown in the previous figures.

FIG. 10 is one example of a computing environment in which elements of FIG. 1, or parts of it, (for example) can be deployed. With reference to FIG. 10, an example system for implementing some embodiments includes a general-purpose computing device in the form of a computer 810. Components of computer 810 may include, but are not limited to, a processing unit 820 (which can comprise processors or servers from any previous Figure), a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. Memory and programs described with respect to FIG. 1 can be deployed in corresponding portions of FIG. 10.

Computer 810 typically includes a variety of computer readable media. Computer readable media can be any available media that can be accessed by computer 810 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 10 illustrates operating system 834, application programs 835, other program modules 836, and program data 837.

The computer 810 may also include other removable/non-removable volatile/nonvolatile computer storage media. By way of example only, FIG. 10 illustrates a hard disk drive 841 that reads from or writes to non-removable, nonvolatile magnetic media, nonvolatile magnetic disk 852, an optical disk drive 855, and nonvolatile optical disk 856. The hard disk drive 841 is typically connected to the system bus 821 through a non-removable memory interface such as interface 840, and optical disk drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 10, provide storage of computer readable instructions, data structures, program modules and other data for the computer 810. In FIG. 10, for example, hard disk drive 841 is illustrated as storing operating system 844, application programs 845, other program modules 846, and program data 847. Note that these components can either be the same as or different from operating system 834, application programs 835, other program modules 836, and program data 837.

A user may enter commands and information into the computer 810 through input devices such as a keyboard 862, a microphone 863, and a pointing device 861, such as a mouse, trackball or touch pad. Other input devices (not shown) may include a joystick, game pad, satellite dish, scanner, or the like. These and other input devices are often connected to the processing unit 820 through a user input interface 860 that is coupled to the system bus, but may be connected by other interface and bus structures. A visual display 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer 810 is operated in a networked environment using logical connections (such as a local area network—LAN, or wide area network WAN) to one or more remote computers, such as a remote computer 880.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules may be stored in a remote memory storage device. FIG. 10 illustrates, for example, that remote application programs 885 can reside on remote computer 880.

It should also be noted that the different examples described herein can be combined in different ways. That is, parts of one or more examples can be combined with parts of one or more other examples. All of this is contemplated herein.

Example 1 is an agricultural machine comprising:
a vibration stimulation source configured to generate a vibration stimulation signal directed toward plant matter;
a sensor system configured to:
sense electromagnetic radiation reflected from the plant matter;
generate a first signal based on the sensed electromagnetic radiation; and
generate a second signal indicative of a resonant vibration response of the plant matter, that is in response to the vibration stimulation signal;
a plant evaluation system configured to:
based on the first and second signals, generate plant characterization data indicative of one or more physical characteristics of the plant matter; and
a control system configured to generate an action signal based on the plant characterization data.

Example 2 is the agricultural machine of any or all previous examples, wherein the control system is configured to send the action signal to at least one of:
a display device, wherein the action signal controls the display device to display an indication of the one or more physical characteristics;
a storage device, wherein the action signal controls the storage device to store an indication of the one or more physical characteristics; or
a controllable machine subsystem, wherein the action signal controls the controllable machine subsystem to perform an agricultural operation relative to the plant matter.

Example 3 is the agricultural machine of any or all previous examples, wherein the control system is configured to send the action signal to a controllable machine subsystem to perform an agricultural operation that applies an agricultural substance to the plant matter.

Example 4 is the agricultural machine of any or all previous examples, wherein the agricultural substance comprises at least one of water or a chemical.

Example 5 is the agricultural machine of any or all previous examples, wherein the controllable machine subsystem comprises a sprayer mechanism and the agricultural operation comprises a spraying operation.

Example 6 is the agricultural machine of any or all previous examples, wherein the control system is configured to send the action signal to a controllable machine subsystem to perform a harvesting operation.

Example 7 is the agricultural machine of any or all previous examples and further comprising:
a location sensor configured to generate an indication of a geographical location of the plant matter; and
a geographical correlation component that correlates the plant characterization data to the geographical location.

Example 8 is the agricultural machine of any or all previous examples, wherein the first signal is indicative of at least one of:
a shape of the plant matter, a location of the plant matter, or a color of the plant matter, and
the one or more physical characteristics comprises at least one of:
a plant species, a plant health, a plant yield, or a number of plants of a particular species.

Example 9 is the agricultural machine of any or all previous examples, wherein the vibration stimulation signal comprises an acoustic signal.

Example 10 is the agricultural machine of any or all previous examples, wherein the sensor system comprises a laser vibrometer configured to generate the second signal.

Example 11 is the agricultural machine of any or all previous examples, wherein the sensor system comprises an imaging sensor configured to capture one or more images of the plant matter by sensing the electromagnetic radiation.

Example 12 is the agricultural machine of any or all previous examples, wherein the first signal is based on a first image of the plant matter, and the second signal is based on a time series of images of the plant matter.

Example 13 is the agricultural machine of any or all previous examples, wherein the agricultural machine comprises a drone.

Example 14 is the agricultural machine of any or all previous examples, wherein the agricultural machine comprises a handheld computing device.

Example 15 is a method performed by an agricultural machine, the method comprising:

generating, by a vibration stimulation source associated with the agricultural machine, a vibration stimulation signal directed toward plant matter;
sensing electromagnetic radiation reflected from the plant matter;
generating a first signal based on the sensed electromagnetic radiation; and
generating a second signal indicative of a resonant vibration response of the plant matter to the vibration stimulation signal;
based on the first and second signals, generating plant characterization data indicative of one or more physical characteristics of the plant matter; and
generating an action signal based on the plant characterization data.

Example 16 is the method of any or all previous examples, wherein
the first signal is indicative of at least one of:
a shape of the plant matter, a location of the plant matter, or a color of the plant matter, and
the one or more physical characteristics comprises at least one of:
a plant species, a plant health, a plant yield, or a number of plants of a particular species.

Example 17 is the method of any or all previous examples, wherein the vibration stimulation signal comprises an acoustic signal, and the second signal generated based on at least one of:
an output from a laser vibrometer that senses the plant matter; or
one or more images of the plant matter captured by an imaging sensor.

Example 18 is the method of any or all previous examples, wherein the first signal is based on a first image of the plant matter, and the second signal is based on a time series of images of the plant matter.

Example 19 is the method of any or all previous examples, and further comprising:
sending the action signal to a controllable machine subsystem to perform an agricultural operation relative to the plant matter Example 20 is an agricultural machine comprising:
a vibration stimulation source configured to generate a vibration stimulation signal directed toward plant matter;
at least one processor; and
memory storing instructions executable by the at least one processor, wherein the instructions when executed, configure the agricultural machine to:
detect a resonant vibration response of the plant matter, that is in response to the vibration stimulation signal;
based on the detected resonant vibration response, generate a plant characterization signal indicative of a physical characteristic of the plant matter, the physical characteristic comprising at least one of:
a plant species, a plant yield, or a number of plants of a particular species; and
generate an action signal based on the plant characterization signal.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An agricultural machine comprising:
a stimulation source configured to generate a vibration stimulation signal, transmitted through air, that mechanically stimulates plant matter on a field;
a sensor system configured to:
sense electromagnetic radiation reflected from the plant matter;
generate a first signal based on the sensed electromagnetic radiation; and
sense a physical response of the plant matter to the vibration stimulation signal;
a plant evaluation system configured to:
obtain prior response data indicative of at least one of structure or condition of a particular plant species;
generate first and second plant characterization data based on:
the sensed physical response of the plant matter to the mechanical stimulation of the plant matter, and
the first signal, wherein
the first plant characterization data identities that a particular plant is of the particular plant species,
the second plant characterization data identities an additional physical characteristic of the particular plant, in addition to plant species, and
one or more of the first plant characterization data and the second plant characterization data is generated based on correlating the sensed physical response with the prior response data; and
a control system configured to generate an action signal based on one or more of the first and second plant characterization data.

2. The agricultural machine of claim 1, wherein the control stem is configured to send the action signal to at least one of:
a display device, wherein the action signal controls the display device to display an indication of one or more of the first and second plant characterization data;
a storage device, wherein the action signal controls the storage device to store an indication of one or more of the first and second plant characterization data; or
a controllable machine subsystem, wherein the action signal controls the controllable machine subsystem to perform an agricultural operation relative to the plant matter.

3. The agricultural machine of claim 1, wherein the control system is configured to send the action signal to a controllable spraying subsystem to perform a spraying operation that applies an agricultural substance to at least a portion of the plant matter.

4. The agricultural machine of claim 1, wherein the physical response comprises a resonant vibration response, and the first plant characterization data is generated based on at least one of a magnitude or a gradient of the resonant vibration response.

5. The agricultural machine of claim 1, wherein the plant evaluation system is configured to generate the second plant characterization data based on correlating the sensed physical response with the prior response data.

6. The agricultural machine of claim 1, wherein the additional physical characteristic indicates a yield of the particular plant.

7. The agricultural machine of claim 1, wherein the additional physical characteristic indicates a health of the particular plant.

8. The agricultural machine of claim 1, wherein the plant evaluation system is configured to distinguish between a plurality of plants of the particular plant species, and generate plant characterization data indicative of different sets of characteristics of each plant in the plurality of plants.

9. The agricultural machine of claim 1, wherein the vibration stimulation signal comprises an acoustic wave, and the physical response comprises a vibration response.

10. The agricultural machine of claim 1, wherein the control system is configured to send the action signal to a controllable machine subsystem configured to perform a harvesting operation.

11. The agricultural machine of claim 1, wherein the sensor system comprises:
   an imaging sensor configured to capture one or more images of the plant matter by sensing the electromagnetic radiation; and
   a laser vibrometer configured to sense the physical response of the plant matter.

12. The agricultural machine of claim 11, wherein the first signal is based on an image of the plant matter, and the physical response of the plant matter is determined based on a time series of images of the plant matter.

13. The agricultural machine of claim 1, wherein the agricultural machine comprises at least one of a drone or a handheld computing device.

14. The agricultural machine of claim 6, wherein the plant evaluation system is configured to determine, based on the first signal, at least one of:
   a shape of the particular plant, a location of the particular plant, or a color of the particular plant;
   and further comprising:
      a location sensor configured to generate an indication of a geographical location of the particular plant; and
      a geographical correlation component that correlates the first plant characterization data to the geographical location.

15. A method performed by an agricultural machine, the method comprising:
   generating, by a stimulation source associated with the agricultural machine, a mechanical wave, transmitted through air, that mechanically stimulates plant matter on a field;
   sensing electromagnetic radiation reflected from the plant matter;
   generating, a first signal based on the sensed electromagnetic radiation;
   determining, based on the first signal, at least one of a shape of the plant matter, a location of the plant matter, or a color of the plant matter;
   detecting a physical response of the plant matter to the mechanical wave;
   generating first plant characterization data that identifies a particular plant species of a particular plant in the plant matter based on correlating the detected physical response of the plant matter with prior response data correlated to the particular plant species, the prior response data being indicative of at least one of structure or condition of the particular plant species;
   generating second plant characterization data based on correlating the detected physical response of the plant matter with the prior response data, wherein the second plant characterization data is indicative of at least one of:
      a plant health, a plant yield, or a number of plants of the particular plant species; and
   generating an action signal based on at least one of the first plant characterization data or the second plant characterization data.

16. The method of claim 15, wherein the physical response is detected based on at least one of:
   an output from a laser vibrometer that senses the plant matter; or
   one or more images of the plant matter captured by an imaging sensor.

17. The method of claim 15, wherein the first signal is based on a first image of the plant matter, and the physical response is detected based on a time series of images of the plant matter.

18. The method of claim 15, wherein
   the physical response comprises a resonant vibration response, and
   the first plant characterization data is generated based on correlating at least one of a magnitude or a gradient of the resonant vibration response with the prior response data.

19. An agricultural machine comprising:
   an acoustic source configured to generate an acoustic wave, transmitted though air, that mechanically stimulates plant matter on a field;
   at least one processor; and
   memory storing instructions executable by the at least one processor, wherein the instructions when executed, configure the agricultural machine to:
      detect a physical response of the plant matter, that is in response to the acoustic wave;
      identify prior response data indicative of at least one of structure or condition of a particular plant species;
      generate first plant characterization data that identifies a plant species of a particular plant in the plant matter based on correlating the detected physical response with the prior response data;
      generate second plant characterization data that identifies an additional physical characteristic of the particular plant, in addition to plant species, wherein one or more of the first plant characterization data or the second plant characterization data is generated based on correlating the detected physical response with the prior response data; and
      generate an action signal based on one or more of the first plant characterization data of the second plant characterization data.

* * * * *